(12) United States Patent
Larue

(10) Patent No.: US 10,890,677 B2
(45) Date of Patent: Jan. 12, 2021

(54) SYSTEM AND METHOD FOR SOIL MOISTURE MONITORING AND IRRIGATION MAPPING

(71) Applicant: Valmont Industries, Inc., Omaha, NE (US)

(72) Inventor: Jacob L. Larue, Omaha, NE (US)

(73) Assignee: Valmont Industries, Inc., Omaha, NE (US)

( * ) Notice: Subject to any disclaimer, the term of this patent is extended or adjusted under 35 U.S.C. 154(b) by 429 days.

(21) Appl. No.: 15/974,885

(22) Filed: May 9, 2018

(65) Prior Publication Data

US 2018/0341032 A1 Nov. 29, 2018

Related U.S. Application Data

(60) Provisional application No. 62/511,414, filed on May 26, 2017.

(51) Int. Cl.
*G01T 3/00* (2006.01)
*G01N 23/20* (2018.01)
*G01N 33/24* (2006.01)
*A01G 25/16* (2006.01)

(52) U.S. Cl.
CPC .............. *G01T 3/008* (2013.01); *A01G 25/16* (2013.01); *G01N 23/20* (2013.01); *G01N 33/246* (2013.01)

(58) Field of Classification Search
CPC ................................ G01T 3/008; G01N 23/20
USPC .................................................... 250/390.05
See application file for complete search history.

(56) References Cited

U.S. PATENT DOCUMENTS

| 2002/0130268 A1* | 9/2002 | Odom | G01T 3/06 250/390.11 |
| 2008/0087837 A1 | 4/2008 | Desilets et al. | |
| 2011/0313577 A1 | 12/2011 | Anderson | |
| 2017/0339851 A1* | 11/2017 | Miller | A01G 25/092 |

OTHER PUBLICATIONS

Jiao et al., "Theory and application of measuring mesoscale soil moisture by cosmic-ray fast neutron probe", IOP Conf. Series: Earth and Environmental Science, 17(2014) 012147 (Year: 2014).*

(Continued)

*Primary Examiner* — David P Porta
*Assistant Examiner* — Abra S Fein
(74) *Attorney, Agent, or Firm* — Milligan PC LLO

(57) ABSTRACT

To address the shortcomings presented in the prior art, the present invention provides a system and method to provide improved irrigation management through the detection of fast neutrons. According to a preferred embodiment, the fast neutron detector of the present invention includes a 4-He based noble gas detector, a power source, a signal processing circuit, and a resistor in series with a preamplifier and a shaping amplifier to produce a processed signal. According to a further preferred embodiment, the present invention preferably further includes a signal channel analyzer and a pulse counter/rate meter. According to a further preferred embodiment, the present invention includes a controller which receives a count of detected fast neutrons and translates the detected number of fast neutrons into an irrigation map indicating the required levels of irrigation needed for selected areas of a given field based on the detected moisture levels.

1 Claim, 3 Drawing Sheets

(56) References Cited

OTHER PUBLICATIONS

Desilets, D et al. "Nature's neutron probe: Land surface hydrology at an elusive scale with cosmic rays" Water Resources Research, vol. 46, Nov. 3, 2010, 7 pgs.

Dong, Jingnou et al. "Calibration and Validation of the COSMOS Rover for Surface Soil Moisture Measurement" Vadose Zone Journal, Apr. 17, 2014, 8 pgs.

* cited by examiner

SYSTEM AND METHOD FOR SOIL MOISTURE MONITORING AND IRRIGATION MAPPING

RELATED APPLICATIONS

The present application claims priority to U.S. Provisional Application No. 62/511,414 filed May 26, 2017.

BACKGROUND AND FIELD OF THE PRESENT INVENTION

1. Field of the Present Invention

The present invention relates generally to a system and method for irrigation management and, more particularly, to a system and method for soil moisture monitoring and irrigation mapping.

2. Background of the Invention

Determining irrigation management zones typically is based on the farmer/operator's knowledge, NRCS soil maps or electro conductivity mapping using Dual EM or Veris type devices. Each has limitations either in resolution or inability to map frozen ground, dependent on soil moisture content and cannot map the field if a crop is present.

Knowing the status of soil water content is a challenge for owners and operators irrigating with center pivot and linear irrigation machines. Soil water content levels in a field are determined by utilizing manual or various types of instruments installed in the field. In most cases the soil water content data is not easily transferred into a useable form for decision making by the irrigation equipment operator.

Manually monitoring soil water content is time consuming and does not provide a good view of the soil water content status across an entire field. Further, to do a good job of soil water content monitoring in many fields requires three, four or more soil moisture sensors or, if collecting manually, a lot of walking. In either case, moisture data in present systems is not readily available for use by owners or operators, nor is it in an easy to use form.

Further, even where multiple moisture sensors are used, the actual area and depth of the soil where the soil water content is measured is limited. Accordingly, the data cannot be used to accurately map the status of an entire field nor can it be used to develop a field wide irrigation strategy for center pivot or linear irrigation equipment. In addition, to do a reasonably good job of monitoring soil water content it becomes expensive due to the equipment cost, installation cost and the probability that one or more of the soil moisture sensors is installed incorrectly or in a spot of the field that is not representative of the general area.

An important new technology for sensing moisture conditions is the fast neutron sensor, commonly referred to as a "COSMOS probe." COSMOS probes work by measuring fast neutron activity near a given surface. These fast neutrons are generated by the impact of secondary cosmic rays with soil. Upon impact, the fast neutrons of the cosmic rays are scattered ("thermalized") and absorbed by the soil. However, some of these fast neutrons escape back into the air above the ground.

The number of fast neutrons escaping any given soil depends on the composition of the soil and, in particular, on its water content. In drier soil, more neutrons escape and in moister soil, less neutrons escape.

To date, the use of COSMOS probes has been limited to static probes which are installed on poles and which are designed to measure the moisture content in a given field over set periods of time. Alternately, they have been used on non-farm work related vehicles for scientific measurements of groundwater concentrations. However, COSMOS probes have not been used to date on farming equipment or movable irrigation systems.

SUMMARY OF THE PRESENT INVENTION

To address the shortcomings presented in the prior art, the present invention provides a system and method for improved irrigation management through the detection of fast neutrons. According to a preferred embodiment, the present invention includes a controller which receives a count of detected fast neutrons and translates the detected number of fast neutrons into an irrigation map indicating the required levels of irrigation needed for selected areas of a given field.

According to a further preferred embodiment, the present invention includes a GPS location detector; a machine orientation detector; an accelerometer and a fast neutron detector. According to a further preferred embodiment, the fast neutron detector of the present invention includes a 4-He based noble gas detector; a power source; a signal processing circuit, and a resistor in series with a preamplifier and a shaping amplifier to produce a processed signal. According to a further preferred embodiment, the present invention preferably further includes a signal channel analyzer and a pulse counter/rate meter.

The accompanying drawings, which are incorporated in and constitute part of the specification, illustrate various embodiments of the present invention and together with the description, serve to explain the principles of the present invention.

DESCRIPTION OF THE PREFERRED EMBODIMENTS

Figure 1:
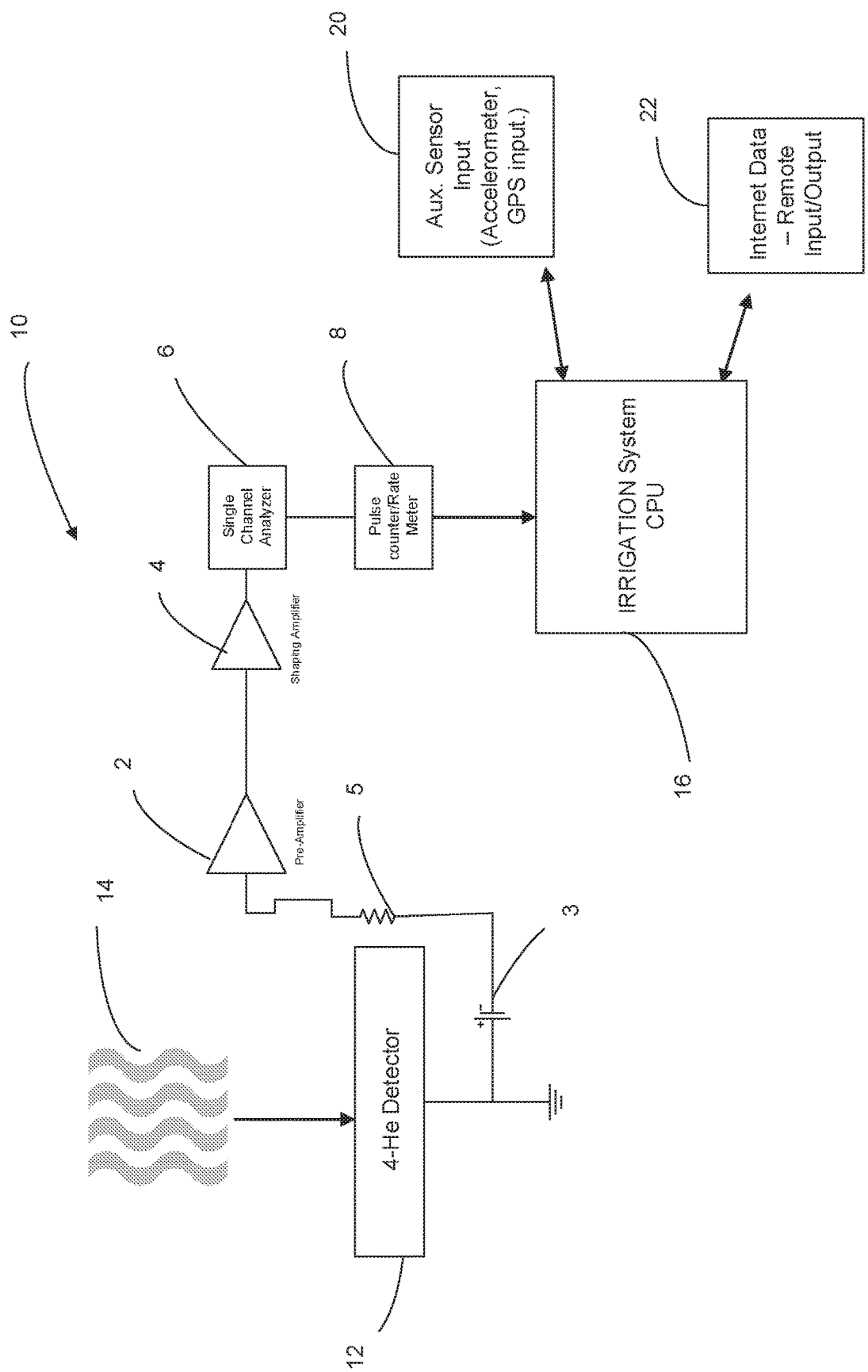
FIG. 1 shows a block diagram of a system in accordance with an embodiment of the present invention.

For the purposes of promoting an understanding of the principles of the present invention, reference will now be made to the embodiments illustrated in the drawings and specific language will be used to describe the same. It will nevertheless be understood that no limitation of the scope of the present invention is hereby intended and such alterations and further modifications in the illustrated devices are contemplated as would normally occur to one skilled in the art.

The terms "program," "computer program," "software application," "module" and the like as used herein, are defined as a sequence of instructions designed for execution on a computer system. A program, computer program, module or software application may include a subroutine, a function, a procedure, an object implementation, an executable application, an applet, a servlet, a source code, an object code, a shared library, a dynamic load library and/or other sequence of instructions designed for execution on a computer system. A data storage means, as defined herein, includes many different types of computer readable media that allow a computer to read data therefrom and that maintain the data stored for the computer to be able to read the data again. Such data storage means can include, for example, non-volatile memory, such as ROM, Flash memory, battery backed-up RAM, Disk drive memory, CD-ROM, DVD, and other permanent storage media. However, even volatile storage such a RAM, buffers, cache memory, and network circuits are contemplated to serve as such data storage means according to different embodiments of the present invention.

With reference now to FIG. 1, a block diagram illustrating an exemplary system 10 of the present invention will now be discussed. As shown in FIG. 1, the present invention includes a fast neutron detector 12 which is preferably tuned to receive a direct reading of the presence of fast neutrons 14. The fast neutron detector 12 of the present invention may preferably be a 4-He based noble gas detector. Alternatively, the fast neutron detector 12 may preferably be a neutron-sensitive scintillating glass fiber detector or another detector design without limitation. As further shown, the fast neutron detector 12 of the present invention preferably includes a signal processing circuit which may include at least a power source 3 and a resistor 5 in series with a preamplifier 2 and a shaping amplifier 4. According to a preferred embodiment, the signal processing circuit preferably amplifies, filters and processes the signal from the detector 12. As further shown, the signal from the shaping amplifier 4 may preferably then be provided to a signal channel analyzer 6 and a pulse counter/rate meter 8 to provide a count of detected fast neutrons to the irrigation system CPU 16 for processing and analysis.

As further shown, the fast neutron data from the fast neutron detector 12 is preferably analyzed within the system CPU 16 along with input from other devices and sensors within the irrigation vehicle. Alternatively, the fast neutron data may be analyzed and processed entirely within the fast neutron detector 12 in which case the data output may preferably be a direct moisture reading or other result.

Preferably, the present invention further includes input from auxiliary sensors 20 which preferably may include inputs such as: GPS location data, accelerometer data, vehicle orientation data and the like. Further, the input data may preferably further include remote data inputs 22 which preferably may include data such as internet and remote input/output data. With the input data from the fast neutron detector 12 and the auxiliary sensors 20, the irrigation system CPU 16 preferably analyzes each piece of source data and maps a given field according to measured moisture levels linked with identified locations as discussed with respect to FIG. 2 below.

Figure 2:
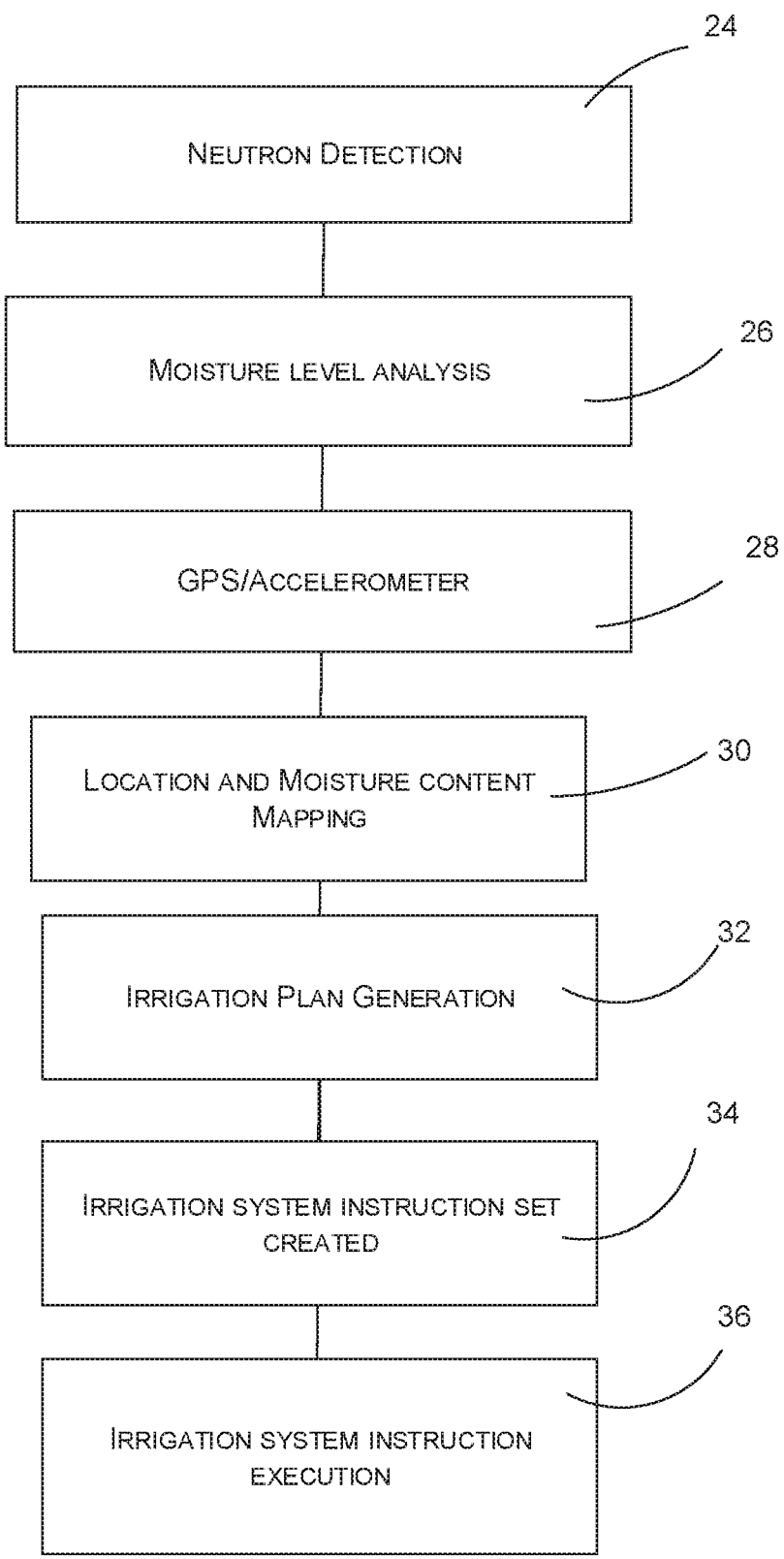
FIG. 2 illustrates a block diagram of an exemplary method for use with the present invention.

With reference now to FIG. 2, an exemplary method and mode of operation in accordance with a first preferred embodiment shall now be discussed. As shown in FIG. 2, at step 24 fast neutron activity is detected. Thereafter, at step 26, the level of fast neutron activity is translated into a moisture reading. As further shown, auxiliary sensor input is received at step 28 preferably including GPS and/or accelerometer data. In step 30, the water content levels are preferably mapped with their GPS measurement points across a given field to be irrigated. With the collected data, the irrigation system CPU 16 preferably creates an irrigation plan at step 32 for the mapped field. Preferably, the created irrigation management zones and irrigation plan includes the detailed water requirements for each area of the mapped field. At step 34, the irrigation system CPU 16 preferably thereafter uses the irrigation plan to generate an irrigation system instruction set for the irrigation system. Preferably, the irrigation system instruction set includes instructions regarding: the movement of the irrigation system; the speed of the irrigation system; and the nozzle settings and the like. In step 36, the instruction set is preferably used by the system CPU 16 to command the actions of the irrigation system.

In accordance with a further preferred embodiment, a system of the present invention may preferably further include a transceiver which allows for the irrigation map, data and plan to be transmitted for further viewing and analysis at a remote location or for use by another irrigation system. According to a preferred embodiment, the irrigation map, data and plan of the present invention may be made available to users or other systems via a smart phone, tablet or any other computing device.

Figure 3:
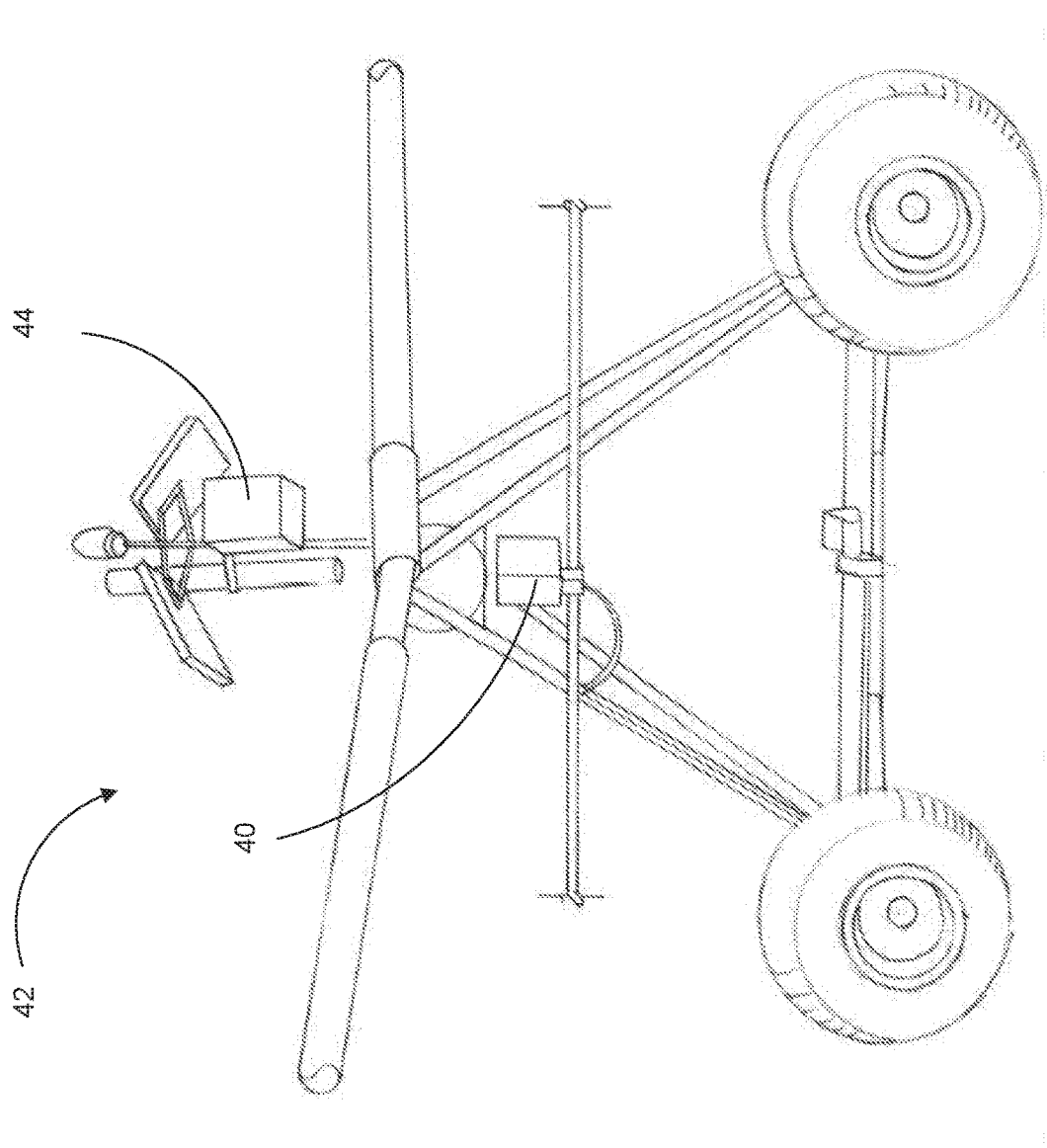
FIG. 3 shows exemplary machinery employing a fast-neutron sensor in accordance with an embodiment of the present invention.

With reference now to FIG. 3, an exemplary irrigation machine 42 employing a fast neutron sensor in accordance with an embodiment of the present invention is shown. As shown, the fast neutron sensor 44 of the present invention can be mounted on an irrigation system 42 which may be linear, center pivot or any other configuration. Accordingly, the present invention uses the movement of the irrigation system to allows the cosmic ray soil moisture sensor(s) to scan an entire field to be irrigated. The fast neutron sensor 44 may be mounted so as to be readily moved from irrigation machine to irrigation machine.

As discussed above, the irrigation control systems 40 of the irrigation system 42 may preferably be controlled and directed with data obtained from the fast neutron sensor 44.

Further, such systems may include controls for adjusting the operating parameters of the irrigation system, such as changing speeds, adjusting sprinkles or modifying irrigation applications. In this way, the system may preferably develop and execute a dynamic irrigation management plan for a target field.

While the above descriptions regarding the present invention contain much specificity, these should not be construed as limitations on the scope, but rather as examples. Many other variations are possible. Accordingly, the scope should be determined not by the embodiments illustrated, but by the appended claims and their legal equivalents.

What is claimed is:

1. A system for detecting and analyzing fast neutron activity to determine soil moisture levels and to direct the actions of an irrigation machine, wherein the system comprises:
    a GPS location detector;
    a machine orientation detector;
    an accelerometer;
    a fast neutron detector, wherein the fast neutron detector is comprised of:
        a 4-He based noble gas detector;
        a power source;
        a signal processing circuit, wherein the signal processing circuit is comprised of a resistor in series with a preamplifier and a shaping amplifier to produce a processed signal;
        a signal channel analyzer, wherein the signal channel analyzer receives the processed signal from the fast neutron detector and isolates signal data from the processed signal; and a pulse counter/rate meter, wherein the pulse counter/rate meter provides a count of the detected fast neutrons from the signal data of the processed signal; and an irrigation system controller, wherein the irrigation system controller receives the count of the detected fast neutrons; further wherein the irrigation system controller further receives GPS coordinates corresponding to the location of the detected fast neutrons; further wherein the irrigation system controller further receives accelerometer data and machine orientation data;

wherein the irrigation system controller translates the detected number of fast neutrons into moisture level data for a given field; further wherein the irrigation system controller combines the moisture level data with the detected GPS coordinates for the detected fast neutrons to create an irrigation map indicating the required levels of irrigation needed for selected areas of the given field based on the detected moisture levels.

\* \* \* \* \*